United States Patent
Yagi et al.

(10) Patent No.: US 10,342,959 B2
(45) Date of Patent: Jul. 9, 2019

(54) BALLOON CATHETER

(71) Applicant: Toray Industries, Inc., Tokyo (JP)

(72) Inventors: Takahiro Yagi, Otsu (JP); Akinori Matsukuma, Otsu (JP); Motoki Takaoka, Otsu (JP); Chigusa Kamemoto, Otsu (JP)

(73) Assignee: Toray Industries, Inc. (JP)

( * ) Notice: Subject to any disclaimer, the term of this patent is extended or adjusted under 35 U.S.C. 154(b) by 306 days.

(21) Appl. No.: 15/129,002

(22) PCT Filed: Mar. 31, 2015

(86) PCT No.: PCT/JP2015/060038
§ 371 (c)(1),
(2) Date: Sep. 26, 2016

(87) PCT Pub. No.: WO2015/152194
PCT Pub. Date: Oct. 8, 2015

(65) Prior Publication Data
US 2017/0128702 A1  May 11, 2017

(30) Foreign Application Priority Data
Mar. 31, 2014 (JP) ................................. 2014-072606

(51) Int. Cl.
*A61M 25/10* (2013.01)
*A61M 25/00* (2006.01)

(52) U.S. Cl.
CPC ..... *A61M 25/1006* (2013.01); *A61M 25/0097* (2013.01); *A61M 2025/1068* (2013.01)

(58) Field of Classification Search
CPC .......... A61M 22/1006; A61M 22/0097; A61M 2025/1068
See application file for complete search history.

(56) References Cited

U.S. PATENT DOCUMENTS

| 4,315,512 A | 2/1982 | Fogarty |
| 5,090,957 A | 2/1992 | Moutafis et al. |

(Continued)

FOREIGN PATENT DOCUMENTS

| JP | 57-501166 A | 7/1982 |
| JP | 58-145648 | 9/1983 |

(Continued)

OTHER PUBLICATIONS

English translation of Notification of Reason for Refusal dated Feb. 26, 2018, of counterpart Korean Application No. 10-2016-7023759.

(Continued)

*Primary Examiner* — Kevin C Sirmons
*Assistant Examiner* — Leah J Swanson
(74) *Attorney, Agent, or Firm* — DLA Piper LLP (US)

(57) ABSTRACT

A balloon catheter includes an inner cylinder shaft having a small-diameter inner cylinder section in a tip side and a large-diameter inner cylinder section in a base-end side; an outer cylinder shaft with the inner cylinder shaft in its lumen; a balloon whose tip is fixed at a tip of the inner cylinder shaft, and whose base end is fixed at the tip of the outer cylinder shaft, wherein the outer cylinder shaft and the inner cylinder shaft slide over each other and cause a shape change between a normal balloon shape and an extended balloon shape; and a housing communicating with the lumen of the outer cylinder shaft, and having a small-diameter lumen in the tip side and a large-diameter lumen in the base-end side; wherein the housing has an insertion inlet for insertion of the inner cylinder shaft, and a liquid inlet/outlet.

16 Claims, 3 Drawing Sheets

(56) References Cited

U.S. PATENT DOCUMENTS

| | | | |
|---|---|---|---|
| 5,769,786 A | | 6/1998 | Wiegel |
| 5,795,325 A | * | 8/1998 | Valley .............. A61B 17/12022 |
| | | | 604/103.1 |
| 5,807,330 A | * | 9/1998 | Teitelbaum ............. A61F 2/958 |
| | | | 604/509 |
| 6,926,729 B1 | | 8/2005 | Sell et al. |
| 2005/0027246 A1 | * | 2/2005 | Dion ................. A61M 25/1018 |
| | | | 604/99.02 |
| 2011/0125132 A1 | * | 5/2011 | Krolik ............. A61B 17/22032 |
| | | | 604/509 |
| 2012/0078096 A1 | | 3/2012 | Krolik et al. |
| 2012/0226341 A1 | * | 9/2012 | Schreck ................. A61F 2/966 |
| | | | 623/1.12 |

FOREIGN PATENT DOCUMENTS

| | | |
|---|---|---|
| JP | H9-206285 A | 8/1997 |
| JP | 2001-518808 A | 10/2001 |
| JP | 2004-305251 A | 11/2004 |
| JP | 2009-526610 A | 7/2009 |
| JP | 2013-500082 A | 1/2013 |
| WO | 98/26833 A1 | 6/1998 |
| WO | 2013/105091 A1 | 7/2013 |

OTHER PUBLICATIONS

Supplementary European Search Report dated Nov. 8, 2017, of counterpart European Patent Application No. 15773663.8.

* cited by examiner

BALLOON CATHETER

TECHNICAL FIELD

This disclosure relates to a balloon catheter.

BACKGROUND

Balloon catheters are medical instruments used in a wide range of fields including percutaneous transluminal angioplasty, percutaneous transluminal coronary angioplasty, and ablation. In general, when a balloon catheter is used for treatment, insertion of the balloon catheter is carried out after protecting the balloon catheter with a tubular protection member called a guiding sheath or the like to allow easy insertion into the body and reduce passage resistance.

In that process, to avoid damaging the balloon by the protection member, the balloon of the balloon catheter is, for example, kept in a thin, deflated state during its insertion into the protection member. As a mechanism for transformation of the balloon, a balloon transformation mechanism having a structure comprising an inner cylinder shaft welded to the balloon tip and an outer cylinder shaft welded to the balloon base end, wherein, by sliding the inner cylinder shaft and the outer cylinder shaft over each other to change the shape of the balloon from an inflatable shape to a thin, deflated shape, insertion and passage of the balloon into the protection member can be facilitated, has been reported (JP 2004-305251 A).

In the balloon transformation mechanism described in JP '251, after the balloon catheter reaches the treatment site, an operation of sliding the inner cylinder shaft needs to be carried out to change the shape of the balloon from the thin, deflated shape to the inflatable shape. However, since the state of the balloon at the tip of a catheter placed in the body cannot be visually observed unless X-ray fluoroscopy or MRI is carried out, there is a possibility that the operation of sliding the inner cylinder shaft is skipped by mistake, followed by the subsequent operation using the balloon having a thin, deflated shape. In such a case, rupture of the balloon might occur due to forced inflation of the balloon having the thin, deflated shape when a liquid is allowed to flow into the balloon in this state, or the treatment might be carried out using the balloon having a shape which is not suitable for the treatment.

In view of this, it could be helpful to provide a balloon catheter having a mechanism that blocks flow of a liquid into the balloon when the balloon has a thin, deflated shape.

SUMMARY

We thus provide:

(1) A balloon catheter comprising: an inner cylinder shaft having a small-diameter inner cylinder section in the tip side and a large-diameter inner cylinder section in the base-end side; an outer cylinder shaft in which the inner cylinder shaft is inserted in its lumen; a balloon whose tip is fixed at the tip of the inner cylinder shaft, and whose base end is fixed at the tip of the outer cylinder shaft, wherein the outer cylinder shaft and the inner cylinder shaft slide over each other to cause a shape change between a normal balloon shape and an extended balloon shape; and a housing which communicates with the lumen of the outer cylinder shaft, and has a small-diameter lumen in the tip side and a large-diameter lumen in the base-end side; wherein the housing has an insertion inlet for insertion of the inner cylinder shaft, and a liquid inlet/outlet for allowing a liquid to flow into, and to flow out of, the balloon and the outer cylinder shaft, and, by inserting the large-diameter inner cylinder section into the small-diameter lumen of the housing when the balloon has the extended balloon shape, inflow of the liquid into the balloon is blocked.

(2) The balloon catheter according to (1), wherein the small-diameter lumen and the large-diameter inner cylinder section have shapes satisfying Formula (1):

$$(A-B)/2 < 0.11 \tag{1}$$

A: inner diameter (mm) of the small-diameter lumen
B: outer diameter (mm) of the large-diameter inner cylinder section.

(3) The balloon catheter according to (1) or (2), wherein the tip of the large-diameter inner cylinder section has an elastic member.

(4) The balloon catheter according to any one of (1) to (3), wherein the large-diameter cylinder section has a projection on its outer periphery, and the small-diameter lumen of the housing has a rail section into which the projection fits on its inner periphery.

(5) The balloon catheter according to any one of (1) to (4), wherein the housing has a see-through section on its side surface, for visual observation of the inside of the housing.

(6) The balloon catheter according to any one of (1) to (5), wherein the housing has a valve for the insertion inlet, and a recess(es) and/or a protrusion(s) is/are provided on the side surface of the large-diameter inner cylinder section.

A balloon catheter that enables prevention of rupture of a balloon caused by forcing a liquid to flow into the balloon when the balloon has an extended shape, and prevention of treatment using a balloon having a shape which is not suitable for the treatment, can be provided since the balloon catheter has a mechanism that blocks flow of a liquid into the balloon when the balloon has the extended shape.

DESCRIPTION OF SYMBOLS

Figure 1:
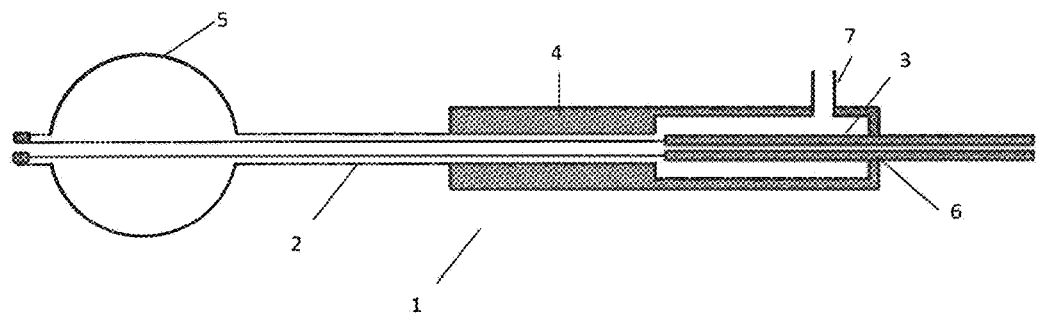
FIG. 1 is a schematic diagram showing a longitudinal cross-sectional view of the balloon catheter according to a first example, wherein the balloon has an inflated shape.

1, Balloon catheter; 2, outer cylinder shaft; 3, inner cylinder shaft; 4, housing; 5, balloon; 6, insertion inlet; 7, liquid inlet/outlet; 10, balloon catheter; 11, projection; 12, rail section; 20, balloon catheter; 21, valve; 30, balloon catheter; 31, recess; 40, balloon catheter; 41, see-through section; 50, elastic member.

DETAILED DESCRIPTION

The balloon catheter comprises: an inner cylinder shaft having a small-diameter inner cylinder section in the tip side and a large-diameter inner cylinder section in the base-end side; an outer cylinder shaft in which the inner cylinder shaft is inserted in its lumen; a balloon whose tip is fixed at the tip of the inner cylinder shaft, and whose base end is fixed at the tip of the outer cylinder shaft, wherein the outer cylinder shaft and the inner cylinder shaft slide over each other to cause a shape change between a normal balloon shape and an extended balloon shape; and a housing which communicates with the lumen of the outer cylinder shaft, and has a small-diameter lumen in the tip side and a large-diameter lumen in the base-end side; wherein the housing has an insertion inlet for insertion of the inner cylinder shaft, and a liquid inlet/outlet allowing a liquid to flow into, and to flow out of, the balloon and the outer cylinder shaft, and, by inserting the large-diameter inner cylinder section into the small-diameter lumen of the housing when the balloon has the extended balloon shape, inflow of the liquid into the balloon is blocked.

Preferred examples are described below in detail with reference to drawings, but this disclosure is not limited to these examples. Each identical element is represented using an identical symbol, and redundant explanations are omitted. The ratios used in the drawings are not necessarily the same as those in the description.

Figure 2:
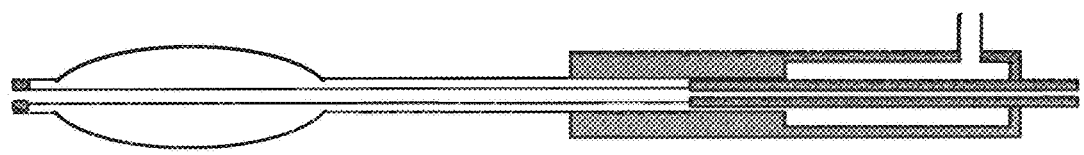
FIG. 2 is a schematic diagram showing a longitudinal cross-sectional view of the balloon catheter according to the first example, wherein the balloon has an extended shape.

A balloon catheter 1 as the first example is shown using FIGS. 1 and 2. FIG. 1 is a longitudinal cross-sectional view of the balloon catheter 1 whose balloon has an inflated shape, and FIG. 2 is a longitudinal cross-sectional view of the balloon catheter 1 whose balloon has an extended shape.

The balloon catheter 1 shown in FIG. 1 has an outer cylinder shaft 2, inner cylinder shaft 3, housing 4, and balloon 5. The outer cylinder shaft 2 is a cylindrical shaft, and has a structure in which the opening in the base-end side of the cylinder connects to the opening in the tip side of the housing 4 such that the lumen of the outer cylinder shaft 2 communicates with the lumen of the housing 4.

The material of the outer cylinder shaft 2 may be any material as long as the material is used for medical catheter shafts. Examples of the material generally include polymer materials having flexibility such as polyamide resins and polyamide elastomers including nylon 11 and nylon 12; polyolefins including polypropylene/polyethylene; polyesters including polyethylene terephthalate; polyurethane; and vinyl chloride. One of these, or a combination of two or more of these may be used.

The inner cylinder shaft 3 is a cylindrical shaft having a small-diameter inner cylinder section in the tip side and a large-diameter inner cylinder section in the base-end side. In the inner cylinder shaft 3, a step is formed between the small-diameter inner cylinder section and the large-diameter lumen section, and the small-diameter inner cylinder section and the large-diameter inner cylinder section are joined to each other along the same axis to form a cylindrical shaft. By insertion of the inner cylinder shaft 3 into the lumen of the outer cylinder shaft 2 and the lumen of the later-mentioned housing 4, a double-cylindrical catheter shaft is constituted.

The "small-diameter inner cylinder section" is the portion in the inner cylinder shaft where the outer diameter vertical to the longitudinal direction of the cylinder is small, and the "large-diameter inner cylinder section" is the portion in the inner cylinder shaft where the outer diameter vertical to the longitudinal direction of the cylinder is large.

The material of the inner cylinder shaft 3 may also be any material as long as the material is used for medical catheter shafts. However, the material of the small-diameter inner cylinder section forming the tip side, similarly to the material of the outer cylinder shaft, is preferably a polymer material having flexibility such as a polyamide resin, polyamide elastomer, polyolefin, polyester, polyurethane, or vinyl chloride. From the viewpoint of simplifying operation of the inner cylinder shaft and increasing the performance to block inflow of the liquid into the balloon, the material of the large-diameter inner cylinder section forming the base-end side is preferably a metal, more preferably stainless steel.

The housing 4 is a cylindrical member having a lumen communicating with the lumen of the outer cylinder shaft 2. The lumen in the tip side along the longitudinal direction has a decreased diameter to form a small-diameter lumen, and the lumen in the base-end side along the longitudinal direction has an increased diameter to form a large-diameter lumen. A step is formed between the small-diameter lumen and the large-diameter lumen, and the small-diameter lumen and the large-diameter lumen communicate with each other to form a lumen inside the housing 4. The cross-sectional shape of the lumen of the housing 4 is not limited. The cross-sectional shape is preferably a circular shape from the viewpoint of continuity with the outer cylinder shaft 2.

At the base end of the cylinder of the housing 4, a bottom surface is formed, and this bottom surface has an insertion inlet 6 for insertion of the inner cylinder shaft 3. The inner cylinder shaft 3 is exposed to the outside of the housing 4 through the insertion inlet 6. By operation of sliding this exposed portion in the longitudinal direction, the later-mentioned operation of changing the shape of the balloon 5 can be carried out.

The outer periphery of the cylinder of the housing 4 has a liquid inlet/outlet 7 that allows a liquid to flow into, and to flow out of, the balloon 5 and the outer cylinder shaft 2. By connecting the liquid inlet/outlet 7 to a syringe, pump, or the like, the liquid can be allowed to flow into the lumen of the housing 4, and can then be allowed to flow into, and to flow out of, the inside of the balloon 5 and the outer cylinder shaft 2 through the lumen of the housing 4.

The material of the housing 4 may be any material as long as the material is is used for medical catheters, and has a strength suitable for the operation. The housing 4 may be made of a metal such as iron or aluminum, or a resin such as a polycarbonate or ABS.

The balloon 5 is formed as a film-shaped member, and has a structure in which the tip of the balloon 5 is fixed to the tip of the inner cylinder shaft 3, and the base end of the balloon 5 is fixed to the tip of the outer cylinder shaft 2. By this, the space inside the balloon 5 communicates with the lumen of the housing 4 through the space formed between the outer cylinder shaft 2 and the inner cylinder shaft 3. The shape of the balloon 5 can be changed between a normal balloon shape and an extended balloon shape by sliding the outer cylinder shaft 2 and the inner cylinder shaft 3 over each other concentrically in the longitudinal direction. Further, by allowing a liquid to flow into the balloon having a normal balloon shape, the shape of the balloon is changed from the normal balloon shape to the inflated balloon shape.

The "normal balloon shape" is a shape of the balloon 5 formed by sliding the inner cylinder shaft 3 toward the base-end side in the longitudinal direction of the outer cylinder shaft 2, wherein inflation of the film forming the balloon 5 is possible by inflow of the liquid. The "extended balloon shape" is an elongated shape of the balloon 5 formed upon drawing of the film forming the balloon 5 by sliding the inner cylinder shaft 3 toward the tip side in the longitudinal direction of the outer cylinder shaft 2, wherein insertion and passage of the balloon catheter 1 into a protection member or the like are possible. The "inflated balloon shape" is a shape formed by allowing the liquid to flow into the balloon to make the balloon shape expanded relative to the normal shape.

An appropriate outer diameter of the balloon 5 having the inflated balloon shape varies depending on the affected area to which the surgical technique is applied. For example, when the balloon 5 is used for treatment of arrhythmia, its outer diameter is preferably 20 to 40 mm. The shape of the balloon 5 having the inflated balloon shape is preferably a spherical shape, but may also be in a tapered, conical shape. The shape of the balloon 5 is not limited to these.

The material of the balloon 5 may be any material as long as the material is one which is used for medical catheters. From the viewpoint of increasing adhesiveness to the affected tissue, the material is preferably a flexible material such as a polyurethane or a rubber, for example, a synthetic rubber or a natural rubber. From the viewpoint of increasing adhesiveness to the affected tissue, the wall thickness of the balloon 5 is preferably 20 to 150 μm, more preferably 20 to 100 μm.

Examples of the liquid with which the balloon 5 may be filled include physiological saline, contrast media for urography/angiography and cisternography/myelography, and contrast media prepared by diluting their stock solutions with physiological saline.

In the housing 4, the lumen in the tip side along the longitudinal direction forms a small-diameter lumen, and the lumen in the base-end side along the longitudinal direction forms a large-diameter lumen. Therefore, when the inner cylinder shaft 3 slides toward the base-end side along the longitudinal direction of the outer cylinder shaft 2 to let the balloon 5 have the normal balloon shape, the tip portion of the large-diameter inner cylinder section of the inner cylinder shaft 3 is positioned in the large-diameter lumen of the housing 4 so that the liquid can be allowed to flow into, and to flow out of, the inside of the balloon 5 and the outer cylinder shaft 2 through the lumen of the housing 4. On the other hand, when the inner cylinder shaft 3 slides toward the tip side along the longitudinal direction of the outer cylinder shaft 2 to let the balloon 5 have the extended balloon shape, the tip of the large-diameter inner cylinder section of the inner cylinder shaft 3 is positioned in the small-diameter lumen of the housing 4 so that the space between the large-diameter lumen and the small-diameter lumen of the housing 4 is narrowed by the large-diameter inner cylinder section of the inner cylinder shaft 3. Therefore, when the liquid is allowed to flow from the liquid inlet/outlet 7 into, or to flow out of, the inside of the housing 4, the liquid passing through the space between the large-diameter lumen and the small-diameter lumen is blocked. This results in a state where the operator who is sliding the inner cylinder shaft 3 can feel resistance on the hand. Thus, the operator can realize that the balloon 5 does not have a normal balloon shape.

"Blocking of the liquid" means a state where a load is applied to the liquid passing through the space between the large-diameter lumen and the small-diameter lumen of the housing 4 so that the operator who is sliding the inner cylinder shaft 3 can feel resistance on the hand. More specifically, this state means a state where the internal pressure of the housing 4 is not less than 0.100 MPa.

More specifically, to block the flow of the liquid, the shape is preferably one with which the value calculated according to Formula 1 is not more than 0.11. The shape is more preferably one with which the value calculated according to Equation (1) is not more than 0.06.

$$(A-B)/2 \tag{1}$$

A: inner diameter (mm) of the small-diameter lumen

B: outer diameter (mm) of the large-diameter inner cylinder section

Figure 8:
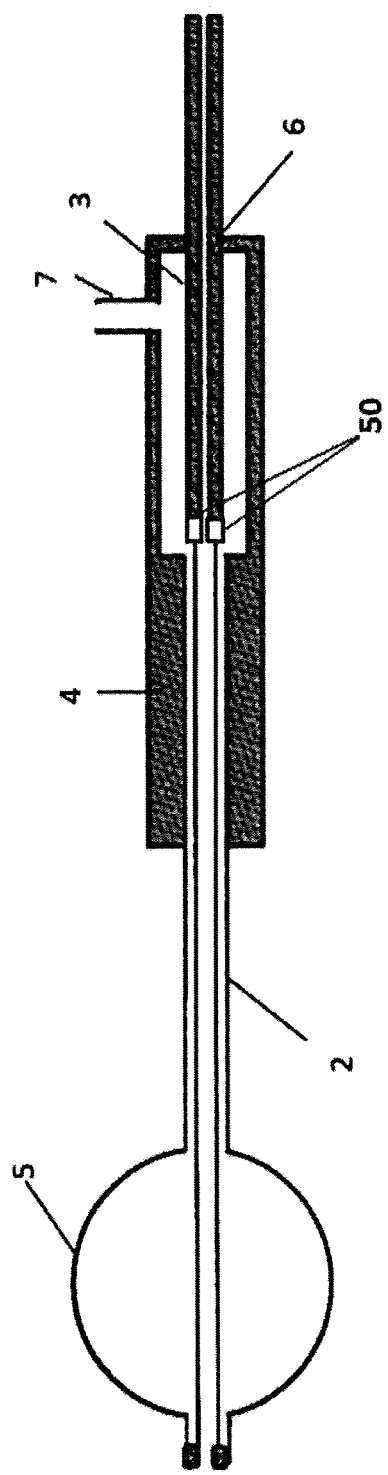
FIG. 8 is a schematic diagram showing a longitudinal cross-sectional view of the balloon catheter according to a fifth example, having an elastic member.

Further, the tip of the large-diameter inner cylinder section of the inner cylinder shaft 3 may have an elastic member 50 as shown in FIG. 8 to block the liquid. The elastic member preferably has a cylindrical shape that covers the tip of the large-diameter inner cylinder section. When the outer diameter of the tip portion of the inner cylinder shaft 3 including the elastic member is larger than the small-diameter lumen of the housing 4, when the elastic member is positioned in the small-diameter lumen of the housing 4, the shape of the elastic member changes such that it fits the shape of the lumen so that the blocking of the flow can be achieved.

From the viewpoint of blocking the flow into the balloon 5, examples of the material of the elastic member include, but are not limited to, natural materials such as sponges; and sponges prepared with synthetic resins such as urethane resins and rubbers.

Figure 3:
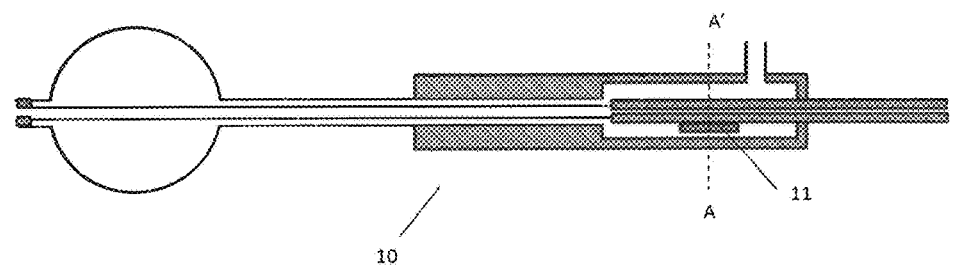
FIG. 3 is a schematic diagram showing a longitudinal cross-sectional view of the balloon catheter according to a second example, wherein the balloon has an inflated shape.
Figure 4:
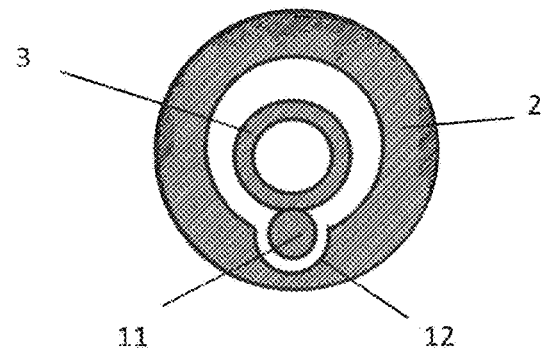
FIG. 4 is a schematic diagram showing a cross-sectional view of the balloon catheter shown in FIG. 3, which cross-sectional view is taken along the A-A' plane, whose direction is vertical to the longitudinal direction.

A balloon catheter 10 as the second example is shown using FIGS. 3 and 4. FIG. 3 is a longitudinal cross-sectional view of the balloon catheter 10 having the inflated balloon shape. FIG. 4 is a cross-sectional view of the balloon catheter 10 shown in FIG. 3, which cross-sectional view is taken along the A-A' plane, whose direction is vertical to the longitudinal direction.

The balloon catheter 10 shown in FIG. 3 has a projection 11 on the large-diameter inner cylinder of the inner cylinder shaft 3. The small-diameter inner cylinder of the housing 4 has a rail section 12 that guides the inner cylinder shaft 3 having the projection 11 when the inner cylinder shaft 3 slides in the longitudinal direction. More specifically, the rail section 12 is a groove carved on the inner periphery of the small-diameter inner cylinder of the housing 4, and is formed such that the projection 11 fits thereinto. The cross-sectional shape of the projection 11 is not limited to a circular shape such as the one shown in FIG. 4, and may be an elliptical shape, diamond shape, triangular shape, quadrangular shape, another kind of polygonal shape, trapezoidal shape, or parallelogram shape. The shape of the rail section 12 may be a circular (elliptical) shape, diamond shape, triangular shape, quadrangular shape, another kind of polygonal shape, trapezoidal shape, or parallelogram shape as long as the projection can be stored therein. The shape of the rail section 12 is preferably similar to the shape of the projection.

By storing the projection 11 in the rail section 12, rolling of the inner cylinder shaft 3 in the housing 4 can be prevented. This shape prevents twisting of the inner cylinder shaft 3, and prevents breakage of the inner cylinder shaft 3 caused by the twisting.

Figure 5:
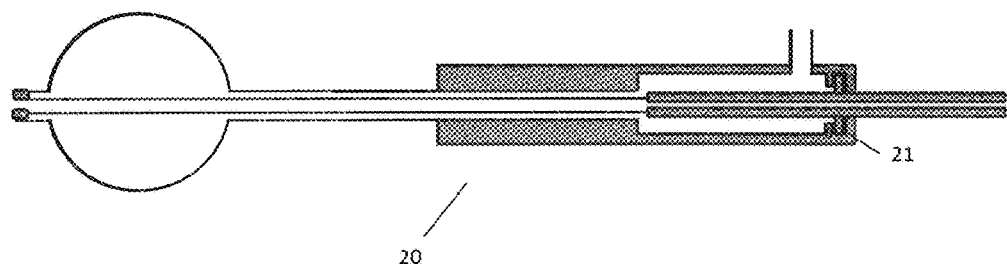
FIG. 5 is a schematic diagram showing a longitudinal cross-sectional view of the balloon catheter according to a third example, wherein the balloon has an inflated shape.

A balloon catheter 20 as the third example is shown using FIG. 5. FIG. 5 is a longitudinal cross-sectional view of the balloon catheter 20 having an inflated balloon shape.

The balloon catheter 20 shown in FIG. 5 has a valve 21 that prevents leakage of the liquid from the insertion inlet 6 on the bottom surface of the housing 4, and prevents inflow of air from the outside of the housing 4. Examples of the shape of the valve 21 include circular shapes, but the shape is not limited as long as leakage of the liquid from the insertion inlet 6 to the outside can be prevented. The valve 21 has a pore, and examples of the shape of the pore include circular shapes. However, the shape of the pore is not limited as long as the pore can hold the inner cylinder shaft 3 in a manner allowing passage of the inner cylinder shaft 3, and also allowing close contact of the inner cylinder shaft 3 with the valve 21 to prevent leakage of the liquid from the lumen of the housing 4 to the outside.

The material of the valve 21 is not limited as long as the material has elasticity, and examples of the material include natural rubbers and silicone resins.

Figure 6:
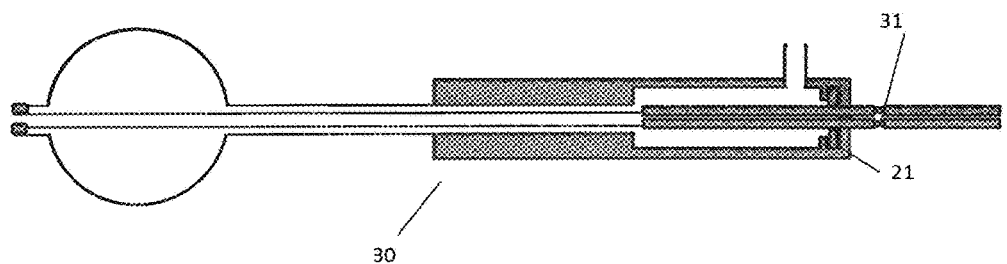
FIG. 6 is a schematic diagram showing a longitudinal cross-sectional view of the balloon catheter according to a fourth example, wherein the balloon has an inflated shape.

A balloon catheter 30 as the fourth example is shown using FIG. 6. FIG. 6 is a longitudinal cross-sectional view of the balloon catheter 30 having an inflated balloon shape.

In the balloon catheter 30 shown in FIG. 6, the housing 4 has a valve 21, and the side surface of the cylinder of the inner cylinder shaft 3 has a recess 31 in the area contacting the valve 21 when the inner cylinder shaft 3 slides over the housing 4. In this mode, a recess 31 having a diameter smaller than the outer diameter of the inner cylinder shaft 3 is used, but a protrusion having a diameter larger than the outer diameter of the inner cylinder shaft 3 may also be used. The recess or the protrusion may be arranged such that a ring is formed on the side surface of the inner cylinder shaft 3, or may be arranged only partially thereon.

Upon sliding of the inner cylinder shaft 3 having the recess 31, the recess 31 contacts the valve 21 to allow the operator to feel resistance on the hand. Thus, by preliminarily knowing the shape of the balloon 5 formed upon the contact of the recess 31 with the valve 21, the operator can recognize the shape of the balloon 5 by feeling the resistance even when the balloon 5 is placed in the body. The base end of the inner cylinder shaft 3 may be provided with a scale. Based on the value indicated by the scale, the shape of the balloon 5 can be recognized.

Figure 7:
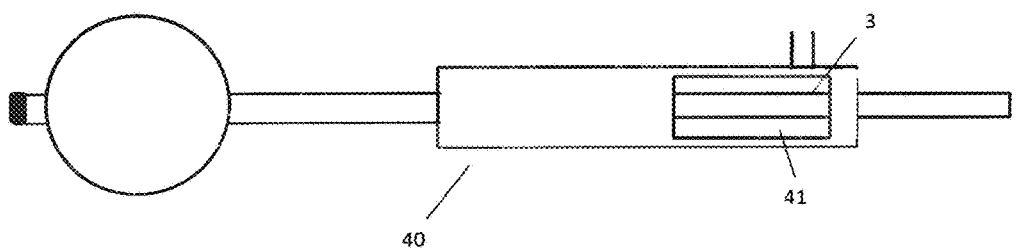
FIG. 7 is a schematic diagram showing a lateral view of the balloon catheter according to a fifth example, wherein the balloon of the balloon catheter has an inflated shape.

A balloon catheter 40 as the fourth example is shown using FIG. 7. FIG. 7 is a schematic diagram showing a lateral view of the balloon catheter 40 having an inflated balloon shape.

The balloon catheter 40 shown in FIG. 7 has a see-through section 41 on the side surface of the housing 4. The see-through section 41 does not necessarily need to be transparent as long as the inside can be visually observed. When air in the lumen of the housing 4 is to be removed, the presence of the air can be seen using the see-through section, and an operation of removing the air can be easily carried out. The surface of the housing 4 is subjected to embossing in some cases for the purpose of suppressing slippage of the hand. In such cases, the lumen could be invisible. When the housing 4 is made of a resin, the see-through section can be secured by providing a portion which is not subjected to the embossing on the side surface of the housing 4. Alternatively, securing the see-through section can be achieved by cutting out a part of the side surface of the housing 4 and fitting a see-through material thereto. The material to be fitted may be any material as long as it is a material through which the inside is visible. Examples of the material include, but are not limited to, resins such as polycarbonate and ABS. The see-through section is preferably positioned near the liquid inlet/outlet. The shape of the see-through section is not limited to a rectangular shape such as the one shown in FIG. 7, and may be a circular shape, elliptical shape, diamond shape, triangular shape, quadrangular shape, another kind of polygonal shape, trapezoidal shape, or parallelogram shape.

EXAMPLES

Specific Examples of our balloon catheters are described below.

Example 1

A balloon catheter according to the example shown in FIG. 5 was prepared as follows.

By a common blow molding method, a polyurethane balloon with an outer diameter of 30 mm and a wall thickness of 20 µm, which balloon has a neck portion with an inner diameter of 3.7 mm, an outer diameter of 4.3 mm, and a length of 3 mm at each of both ends, was prepared. A polyurethane outer cylinder shaft having an outer diameter of 4 mm, an inner diameter of 3 mm, and a length of 905 mm, was prepared.

A polyamide small-diameter inner cylinder section for an inner cylinder shaft, having an outer diameter of 1.8 mm, an inner diameter of 1.4 mm, and a total length of 1100 mm, was prepared. In addition, by molding, a metallic large-diameter inner cylinder section for the inner cylinder shaft, having an outer diameter of 3 mm and a length of 115 mm, was prepared. The surface of the metallic large-diameter inner cylinder section of the inner cylinder shaft was covered with a polyurethane elastic body. By this, the outer diameter became 3.7 mm. The tip of the large-diameter inner cylinder section of the inner cylinder shaft was arranged at a position of 10 mm from the posterior end of the small-diameter inner cylinder section of the inner cylinder shaft, and an adhesive was injected into the gap for fixation, thereby preparing an inner cylinder shaft.

A polycarbonate housing with a total length of 152 mm having a lumen with an inner diameter of 3.62 mm in the area from the tip to a position 74 mm distant from the tip in the longitudinal direction (small-diameter lumen), and a lumen with an inner diameter of 5.27 mm in the area posterior to the position 74 mm distant from the tip in the longitudinal direction (large-diameter lumen), was prepared. On the side surface of the housing, a liquid inlet with an outer diameter of 5.5 mm and an inner diameter of 4.4 mm was provided, and an insertion inlet with an inner diameter of 3.7 mm having a silicone hemostasis valve in the lumen side of the housing was provided on the bottom surface, which corresponds to the posterior end of the housing. An adhesive was applied to the outer periphery of the tip side of the housing, and the posterior end of the outer cylinder shaft was attached thereto.

The inner cylinder shaft was inserted into the lumen of the housing from the posterior end of the housing. The inner cylinder shaft was then allowed to reach the lumen of the outer cylinder shaft, and the tip of the small-diameter inner cylinder section of the inner cylinder shaft and the tip of the tip-side neck portion of the balloon were joined together, followed by fixing the balloon to the outer periphery of the inner cylinder shaft by thermal welding. The tip of the outer cylinder shaft and the root of the posterior end-side neck portion of the balloon were joined together, and the balloon was fixed to the outer periphery of the outer cylinder shaft by thermal welding, to prepare a balloon catheter.

Example 2

A balloon catheter (hereinafter referred to as "Example 2") was prepared in the same manner as in Example 1 except that a metallic large-diameter inner cylinder section for the inner cylinder shaft, having an outer diameter of 3.58 mm, was used instead of the metallic large-diameter inner cylinder section for the inner cylinder shaft of Example 1, and that the treatment of covering the surface with the elastic body was not carried out.

Example 3

A balloon catheter (hereinafter referred to as "Example 3") was prepared in the same manner as in Example 2 except that a metallic large-diameter inner cylinder section for the inner cylinder shaft, having an outer diameter of 3.55 mm, was used instead of the metallic large-diameter inner cylinder section for the inner cylinder shaft of Example 2.

Example 4

A balloon catheter (hereinafter referred to as "Example 4") was prepared in the same manner as in Example 2 except that a metallic large-diameter inner cylinder section for the inner cylinder shaft, having an outer diameter of 3.50 mm, was used instead of the metallic large-diameter inner cylinder section for the inner cylinder shaft of Example 2.

Example 5

A balloon catheter (hereinafter referred to as "Example 5") was prepared in the same manner as in Example 2 except that a metallic large-diameter inner cylinder section for the inner cylinder shaft, having an outer diameter of 3.45 mm, was used instead of the metallic large-diameter inner cylinder section for the inner cylinder shaft of Example 2.

Example 6

A balloon catheter (hereinafter referred to as "Example 6") was prepared in the same manner as in Example 2 except that a metallic large-diameter inner cylinder section for the inner cylinder shaft, having an outer diameter of 3.30 mm, was used instead of the metallic large-diameter inner cylinder section for the inner cylinder shaft of Example 2.

Example 7

A balloon catheter (hereinafter referred to as "Example 7") was prepared in the same manner as in Example 2 except that a metallic large-diameter inner cylinder section for the inner cylinder shaft, having an outer diameter of 3.30 mm, was used instead of the metallic large-diameter inner cylinder section for the inner cylinder shaft of Example 2.

Comparative Example 1

A balloon catheter (hereinafter referred to as "Comparative Example 1") was prepared in the same manner as in Example 2 except that a metallic large-diameter inner cylinder section for the inner cylinder shaft, having an outer diameter of 2.50 mm, was used instead of the metallic large-diameter inner cylinder section for the inner cylinder shaft of Example 2.

Comparative Example 2

A handle (hereinafter referred to as "Comparative Example 2") was prepared in the same manner as in Example 2 except that a metallic large-diameter inner cylinder section for the inner cylinder shaft, having an outer diameter of 3.58 mm, was used instead of the metallic large-diameter inner cylinder section for the inner cylinder shaft of Example 2, and that the position of the tip of the metallic large-diameter inner cylinder section for the inner cylinder shaft was fixed in the large-diameter lumen of the housing.

Measurement of Pressure during Injection of Liquid

To measure the pressure during injection of the liquid, for each balloon catheter prepared in the Examples and the Comparative Examples, an experiment was carried out using the balloon and the inner cylinder shaft excluding the small-diameter inner cylinder section. As liquids, physiological saline, and a diluted contrast medium prepared by diluting a contrast medium with physiological saline, were provided. The diluted contrast medium was prepared as a 1:1 mixture of Hexabrix 320, a commercially available iodinated contrast medium, and physiological saline. To an automatic injector Mark V ProVis (model number, PPD507), manufactured by MEDRAD, 150 mL of each liquid was fed. To the three-way stopcock of the handle, a pressure gauge and the automatic injector were connected. The maximum pressure value during injection of 100 mL of the liquid at 15 mL/second was recorded.

The results are described in Table 1. Since blocking of the flow of the liquid can be felt at not less than 0.100 MPa during manual injection of the liquid, this value was used as the border. As a result, a clearance of not more than 0.11 was evaluated as a preferred condition based on the results obtained by injection of the diluted contrast medium, which has a higher viscosity than physiological saline, and a clearance of not more than 0.06 was evaluated as a more preferred condition based on the results obtained by injection of physiological saline.

TABLE 1

|  | Example 1 | Example 2 | Example 3 | Example 4 | Example 5 | Example 6 | Example 7 | Comparative Example 1 | Comparative Example 2 |
|---|---|---|---|---|---|---|---|---|---|
| Inner diameter (mm) of the small-diameter lumen . . . A | 3.62 | 3.62 | 3.62 | 3.62 | 3.62 | 3.62 | 3.62 | 3.62 | 3.62 |
| Outer diameter (mm) of the large-diameter inner cylinder section . . . B | 3.70 | 3.58 | 3.55 | 3.50 | 3.45 | 3.40 | 3.00 | 2.50 | 3.58 |
| Clearance | 0 (*1) | 0.02 | 0.04 | 0.06 | 0.09 | 0.11 | 0.31 | 0.56 | 1.81 (*2) |

TABLE 1-continued

| | Example 1 | Example 2 | Example 3 | Example 4 | Example 5 | Example 6 | Example 7 | Comparative Example 1 | Comparative Example 2 |
|---|---|---|---|---|---|---|---|---|---|
| [(A − B)/2] Position of the tip of the large-diameter inner cylinder section in the housing | Small-diameter lumen | Small-diameter lumen | Small-diameter lumen | Small-diameter lumen | Small-diameter lumen | Small-diameter lumen | Small-diameter lumen | Small-diameter lumen | Large-diameter lumen |
| Pressure (MPa) during injection of physiological saline | 0.392 | 0.379 | 0.189 | 0.101 | 0.094 | 0.066 | 0.040 | 0.040 | 0.040 |
| Pressure (MPa) during injection of a diluted contrast medium | 0.483 | 0.451 | 0.201 | 0.196 | 0.183 | 0.109 | 0.080 | 0.080 | 0.080 |

(*1) Since, in Example 1, the small-diameter lumen of the housing and the large-diameter inner cylinder section of the inner cylinder shaft are in close contact with each other because of the elastic member, the clearance in Example 1 was regarded as 0.
(*2) Since, in Comparative Example 2, the large-diameter inner cylinder section of the inner cylinder shaft does not reach the small-diameter lumen of the housing, the clearance in Comparative Example 2 was calculated as the inner diameter of the small-diameter lumen of the housing/2.

INDUSTRIAL APPLICABILITY

We provide a balloon catheter that can be easily handled since it prevents rupture of a balloon due to forced feeding of a liquid into the balloon having an extended shape, and also prevents treatment with a balloon having a shape that is not suitable for the treatment.

The invention claimed is:

1. A balloon catheter comprising:
an inner cylinder shaft having a small-diameter inner cylinder section in a tip side and a large-diameter inner cylinder section in a base-end side;
an outer cylinder shaft in which said inner cylinder shaft is inserted in a lumen of said outer cylinder shaft;
a balloon whose tip is fixed at a tip of said inner cylinder shaft, and whose base end is fixed at a tip of said outer cylinder shaft, wherein said outer cylinder shaft and said inner cylinder shaft slide over each other and cause a shape change between a normal balloon shape and an extended balloon shape; and
a housing communicating with the lumen of said outer cylinder shaft, and having a small-diameter lumen in a tip side and a large-diameter lumen in a base end side; wherein
said housing has an insertion inlet for insertion of said inner cylinder shaft, and a liquid inlet/outlet that allows a liquid to flow into, and to flow out of, said balloon and said outer cylinder shaft, and
by inserting said large-diameter inner cylinder section into said small-diameter lumen of said housing when said balloon has said extended balloon shape, inflow of said liquid in said housing is blocked.

2. The balloon catheter according to claim 1, wherein said small-diameter lumen and said large-diameter inner cylinder section have shapes satisfying Formula (1):

$$(A-B)/2 \leq 0.11 \quad (1)$$

A: inner diameter (mm) of the small-diameter lumen
B: outer diameter (mm) of the large-diameter inner cylinder section.

3. The balloon catheter according to claim 2, wherein a tip of said large-diameter inner cylinder section has an elastic member.

4. The balloon catheter according to claim 2, wherein said large-diameter cylinder section has a projection on an outer periphery of said large-diameter cylinder section, and said small-diameter lumen of said housing has a rail section into which said projection fits on an inner periphery of said small-diameter lumen.

5. The balloon catheter according to claim 2, wherein said housing has a see-through section on a side surface of said housing, for visual observation of an inside of said housing.

6. The balloon catheter according to claim 2, wherein said housing has a valve for said insertion inlet, and a recess(es) and/or a protrusion(s) is/are provided on a side surface of said large-diameter inner cylinder section.

7. The balloon catheter according to claim 1, wherein a tip of said large-diameter inner cylinder section has an elastic member.

8. The balloon catheter according to claim 7, wherein said large-diameter cylinder section has a projection on an outer periphery of said large-diameter cylinder section, and said small-diameter lumen of said housing has a rail section into which said projection fits on an inner periphery of said small-diameter lumen.

9. The balloon catheter according to claim 7, wherein said housing has a see-through section on a side surface of said housing, for visual observation of an inside of said housing.

10. The balloon catheter according to claim 7, wherein said housing has a valve for said insertion inlet, and a recess(es) and/or a protrusion(s) is/are provided on a side surface of said large-diameter inner cylinder section.

11. The balloon catheter according to claim 1, wherein said large-diameter cylinder section has a projection on an outer periphery of said large-diameter cylinder section, and said small-diameter lumen of said housing has a rail section into which said projection fits on an inner periphery of said small-diameter lumen.

12. The balloon catheter according to claim 11, wherein said housing has a see-through section on a side surface of said housing, for visual observation of an inside of said housing.

13. The balloon catheter according to claim 11, wherein said housing has a valve for said insertion inlet, and a recess(es) and/or a protrusion(s) is/are provided on a side surface of said large-diameter inner cylinder section.

14. The balloon catheter according to claim 1, wherein said housing has a see-through section on a side surface of said housing, for visual observation of an inside of said housing.

15. The balloon catheter according to claim 14, wherein said housing has a valve for said insertion inlet, and a recess(es) and/or a protrusion(s) is/are provided on a side surface of said large-diameter inner cylinder section.

16. The balloon catheter according to claim 1, wherein said housing has a valve for said insertion inlet, and a recess(es) and/or a protrusion(s) is/are provided on a side surface of said large-diameter inner cylinder section.

* * * * *